US010779716B2

(12) United States Patent
Yabe et al.

(10) Patent No.: US 10,779,716 B2
(45) Date of Patent: Sep. 22, 2020

(54) LIGHT SOURCE SYSTEM, LIGHT SOURCE CONTROL METHOD, FIRST LIGHT SOURCE APPARATUS, AND ENDOSCOPE SYSTEM

(71) Applicant: OLYMPUS CORPORATION, Tokyo (JP)

(72) Inventors: Yusuke Yabe, Chofu (JP); Shuhei Hatanaka, Kobe (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/663,612

(22) Filed: Oct. 25, 2019

(65) Prior Publication Data
US 2020/0060530 A1    Feb. 27, 2020

Related U.S. Application Data

(63) Continuation of application No. PCT/JP2018/006485, filed on Feb. 22, 2018.

(30) Foreign Application Priority Data

Apr. 27, 2017 (JP) .................................. 2017-088688

(51) Int. Cl.
*A61B 1/06* (2006.01)
*H05B 45/10* (2020.01)
(Continued)

(52) U.S. Cl.
CPC .......... *A61B 1/0638* (2013.01); *A61B 1/0002* (2013.01); *A61B 1/00006* (2013.01);
(Continued)

(58) Field of Classification Search
CPC . A61B 1/0638; A61B 1/00006; A61B 1/0002; A61B 1/043; A61B 1/05; A61B 1/0684; H05B 45/10
(Continued)

(56) References Cited

U.S. PATENT DOCUMENTS 5,187,572 A     2/1993  Nakamura et al.
2012/0157775 A1* 6/2012  Yamaguchi ........ A61B 5/14551
                                                       600/180
(Continued)

FOREIGN PATENT DOCUMENTS

JP      05-84218 A      4/1993
JP      2012-130429 A   7/2012
(Continued)

OTHER PUBLICATIONS

International Search Report dated May 22, 2018 received in PCT/JP2018/006485.

*Primary Examiner* — Wei (Victor) Y Chan
(74) *Attorney, Agent, or Firm* — Scully Scott Murphy & Presser

(57) ABSTRACT

A light source system includes a normal light source apparatus provided with a light source controller and a light source apparatus for specific light provided with a specific light controller. In a state where communication is enabled, the light source controller adjusts an emission intensity of the normal light, generates a light amount control signal that makes the normal light and the specific light have a predetermined light amount ratio, and sends the light amount control signal to the light source apparatus for specific light. The specific light controller adjusts an emission intensity of the specific light based on the received light amount control signal.

12 Claims, 10 Drawing Sheets

(51) Int. Cl.
  *A61B 1/00* (2006.01)
  *A61B 1/04* (2006.01)
  *A61B 1/05* (2006.01)

(52) U.S. Cl.
  CPC ............... *A61B 1/043* (2013.01); *A61B 1/05* (2013.01); *A61B 1/0684* (2013.01); *H05B 45/10* (2020.01)

(58) Field of Classification Search
  USPC ............... 348/E5.034, E9.053; 315/76, 153
  See application file for complete search history.

(56) References Cited

U.S. PATENT DOCUMENTS

| | | | |
|---|---|---|---|
| 2015/0287366 A1* | 10/2015 | Miyamoto | G03B 21/2053 345/690 |
| 2016/0092198 A1* | 3/2016 | Vangeel | G05B 19/04 717/173 |
| 2017/0303768 A1* | 10/2017 | Kojima | A61B 1/00045 |

FOREIGN PATENT DOCUMENTS

| | | |
|---|---|---|
| JP | 2015-091417 A | 5/2015 |
| WO | 2013/031701 A1 | 3/2013 |

* cited by examiner

FIG. 4
|  | NORMAL LIGHT OBSERVATION LIGHT SOURCE APPARATUS | SPECIFIC LIGHT OBSERVATION LIGHT SOURCE APPARATUS | VIDEO PROCESSING APPARATUS | NORMAL ENDOSCOPE | SPECIFIC LIGHT OBSERVATION ENDOSCOPE |
|---|---|---|---|---|---|
| NORMAL LIGHT OBSERVATION | ○ | — | ○ | ○ | — |
| NORMAL LIGHT OBSERVATION + SPECIFIC LIGHT OBSERVATION | ○ | ○ | ○ | — | ○ |
FIG. 5
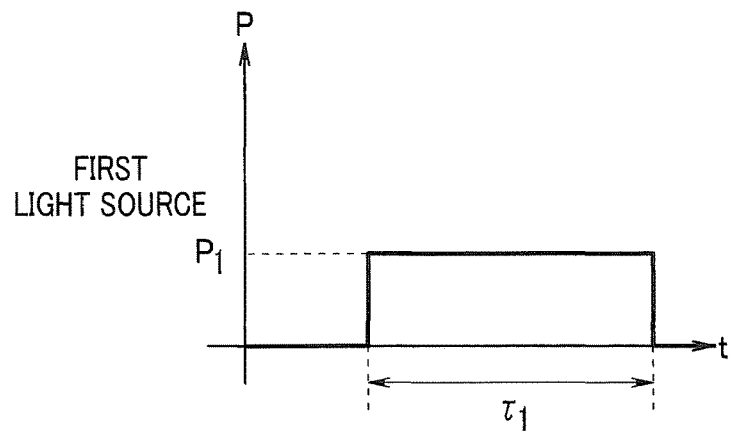
FIG. 6
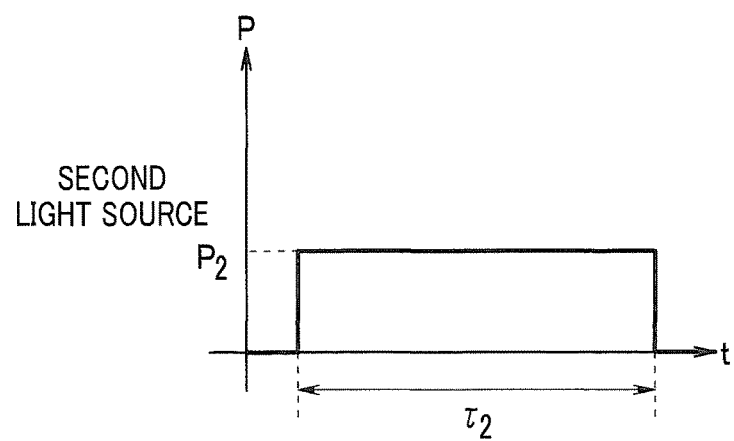

LIGHT SOURCE SYSTEM, LIGHT SOURCE CONTROL METHOD, FIRST LIGHT SOURCE APPARATUS, AND ENDOSCOPE SYSTEM

CROSS REFERENCE TO RELATED APPLICATION

This application is a continuation application of PCT/JP2018/006485 filed on Feb. 22, 2018 and claims benefit of Japanese Application No. 2017-088688 filed in Japan on Apr. 27, 2017, the entire contents of which are incorporated herein by this reference.

BACKGROUND OF THE INVENTION

1. Field of the Invention

The present invention relates to a light source system that can emit a normal light and a specific light, a method for controlling light sources that emit a normal light and a specific light, a first light source apparatus that can generate a first light, and an endoscope system in which a first light and a second light are supplied to an endoscope.

2. Description of the Related Art

Conventionally, there has been proposed a light source apparatus that generates a normal light and a specific light having a different spectrum from a spectrum of the normal light.

For example, Japanese Patent Application Laid-Open Publication No. 2015-91417 describes an illuminating device including: a plurality of semiconductor light sources each of which emits light with a spectrum different from one another; target light amount setting means for setting a target light amount for a total outgoing light amount; light amount ratio setting means for setting an outgoing light amount ratio among the plurality of semiconductor light sources; amplitude value setting means for setting an amplitude value of driving signal for each of the semiconductor light sources on the basis of the set outgoing light amount ratio; and driving signal generating means for generating each driving signal through the use of common pulse modulation control based on the target light amount, while keeping the driving signal at the set amplitude value, wherein when the target light amount is set, a driving pulse signal corresponding to the target light amount is set in common among the semiconductor light sources, and the driving pulse signal is so set at the amplitude values corresponding to the outgoing light amount ratio as to generate individual driving signals for driving the respective semiconductor light sources. It is described that thus, the light amount can be controlled to the target light amount with a high degree of accuracy without losing the balance in the outgoing light amount ratio among the plurality of semiconductor light sources.

International Publication No. 2013/031701 describes an endoscope device comprising: an illumination means for, within a prescribed time, carrying out an illumination by an illumination light of a first band, and carrying out an illumination by an illumination light of a second band over a first number of iterations which is greater than one; a brightness computation means for computing a first brightness by a color conversion matrix process which uses a first image capture signal on the basis of the illumination by the illumination light of the first band and a second image capture signal on the basis of the illumination of a first prescribed iteration among the first number of iterations, and for computing a second brightness by a color conversion matrix process which uses the first image capture signal on the basis of the illumination by the illumination light of the first band and a second image capture signal on the basis of the illumination of other than the first prescribed iteration among the first number of iterations; and a compositing means for multiplying the first and second image capture signals which are the basis of the second brightness by a coefficient based on the ratio of the second brightness to the difference of the first brightness and a target brightness, and thereafter compositing same with the first and second image capture signals which are the basis of the first brightness. It is described that thus, light adjustment control corresponding to the sense of an operator can be performed while image quality degradation is suppressed.

SUMMARY OF THE INVENTION

A light source system according to an aspect of the present invention includes: a normal light source apparatus provided within a housing and configured to be able to emit a normal light to be emitted toward a subject; a light source apparatus for specific light provided independently of the housing and configured to be able to emit a specific light having a different spectrum from a spectrum of the normal light toward the subject; a light source controller provided in the normal light source apparatus and configured to adjust an emission intensity of the normal light and to generate a light amount control signal that makes a light amount of the specific light have a predetermined light amount ratio to a light amount of the normal light; and a specific light controller provided in the light source apparatus for specific light and configured to adjust an emission intensity of the specific light, wherein in a state where communication between the normal light source apparatus and the light source apparatus for specific light is enabled, the light source controller adjusts the emission intensity of the normal light and sends the light amount control signal to the light source apparatus for specific light, and the specific light controller adjusts the emission intensity of the specific light based on the received light amount control signal.

A light source control method according to another aspect of the present invention includes: emitting a normal light toward a subject from a normal light source apparatus provided within a housing; emitting a specific light having a different spectrum from a spectrum of the normal light toward the subject from a light source apparatus for specific light provided independently of the housing; in a state where communication between the normal light source apparatus and the light source apparatus for specific light is enabled, adjusting an emission intensity of the normal light by a light source controller provided in the normal light source apparatus, generating by the light source controller a light amount control signal that makes a light amount of the specific light have a predetermined light amount ratio to a light amount of the normal light, and sending the light amount control signal to the light source apparatus for specific light; and receiving the light amount control signal by a specific light controller provided in the light source apparatus for specific light, and adjusting by the specific light controller an emission intensity of the specific light based on the light amount control signal.

A first light source apparatus according to yet another aspect of the present invention can generate a first light having a first spectral distribution to be emitted toward a subject, and includes: a housing; a first light source provided within the housing and configured to emit the first light; and a light source controller provided within the housing and configured to adjust an emission intensity of the first light source, wherein the first light source apparatus can communicate with a second light source apparatus provided outside the housing, the second light source apparatus including a second light source configured to emit a second light having a second spectral distribution different from the first spectral distribution and a second light controller configured to adjust an emission intensity of the second light source, and in a state where communication between the first light source apparatus and the second light source apparatus is enabled, the light source controller adjusts the emission intensity of the first light source, and sends to the second light source apparatus a light amount control signal for allowing the second light controller to control the second light source and for adjusting the emission intensity of the second light in such a manner as to make a light amount of the second light have a predetermined light amount ratio to a light amount of the first light.

An endoscope system according to still another aspect of the present invention includes: a first light source apparatus provided within a housing and configured to be able to emit a first light having a first spectral distribution to be emitted toward a subject; a second light source apparatus provided independently of the housing and configured to be able to emit a second light having a second spectral distribution different from the first spectral distribution toward the subject; an endoscope connected to the first light source apparatus and the second light source apparatus and configured to be supplied with the first light and the second light to be emitted toward the subject; a light source controller provided in the first light source apparatus and configured to adjust an emission intensity of the first light and to generate a light amount control signal that makes a light amount of the second light have a predetermined light amount ratio to a light amount of the first light; and a second light controller provided in the second light source apparatus and configured to adjust an emission intensity of the second light, wherein in a state where communication between the first light source apparatus and the second light source apparatus is enabled, the light source controller adjusts the emission intensity of the first light and sends the light amount control signal to the second light source apparatus, and the second light controller adjusts the emission intensity of the second light based on the received light amount control signal.

BRIEF DESCRIPTION OF THE DRAWINGS

FIG. 4 is a table showing combinations of apparatuses to be purchased by a user who performs only normal light observation and by a user who performs normal light observation and specific light observation in the first embodiment;

FIG. 5 is a plot showing an example of a light amount of a first light source according to an emission time period and an emission intensity in the first embodiment;

FIG. 6 is a plot showing an example of a light amount of a second light source according to an emission time period and an emission intensity in the first embodiment;

DETAILED DESCRIPTION OF THE PREFERRED EMBODIMENTS

Hereinafter, embodiments of the present invention will be described with reference to drawings.

First Embodiment

Figure 1:
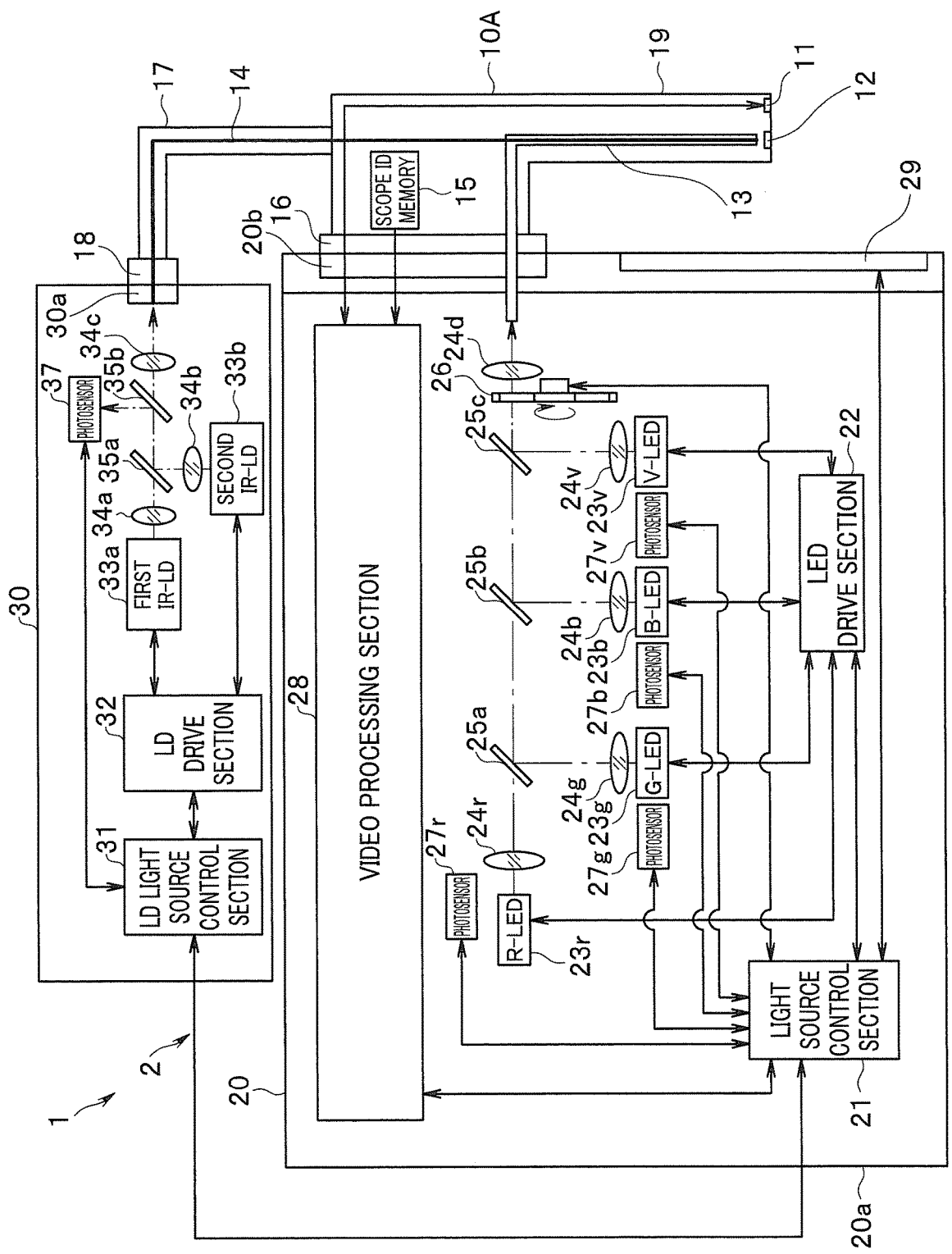
FIG. 1 is a diagram showing an example of a configuration of an endoscope system that can perform observation using a normal light and a specific light, according to a first embodiment of the present invention.

FIGS. 1 to 9 show a first embodiment of the present invention, and FIG. 1 is a diagram showing an example of a configuration of an endoscope system 1 that can perform observation using a normal light and a specific light.

The endoscope system 1 shown in the example of the configuration of FIG. 1 includes a specific light observation endoscope 10A, as well as a normal light source apparatus 20 and a specific light observation light source apparatus 30 that are included in a light source apparatus system 2, and is configured to be able to set an observation mode in any of a white light observation mode, a narrow band observation mode, and a fluorescence observation mode.

The specific light observation endoscope 10A is an endoscope configured to be able to perform both observation using the normal light and observation using the specific light having a different spectrum from a spectrum of the normal light, and including an image pickup unit 11, an illumination lens 12, a light guide 13, a specific light guide 14, a scope ID memory 15, a universal connector 16, a specific light splitter cord 17, a specific light connector 18, and an insertion portion 19.

The image pickup unit 11 is arranged at a distal end portion of the insertion portion 19 of the specific light observation endoscope 10A, and includes an objective lens (not shown) configured to form an optical image of a subject irradiated with the normal light or the specific light, and an image pickup section (see FIG. 2) configured to convert the optical image formed by the objective lens into an electrical signal.

Figure 2:
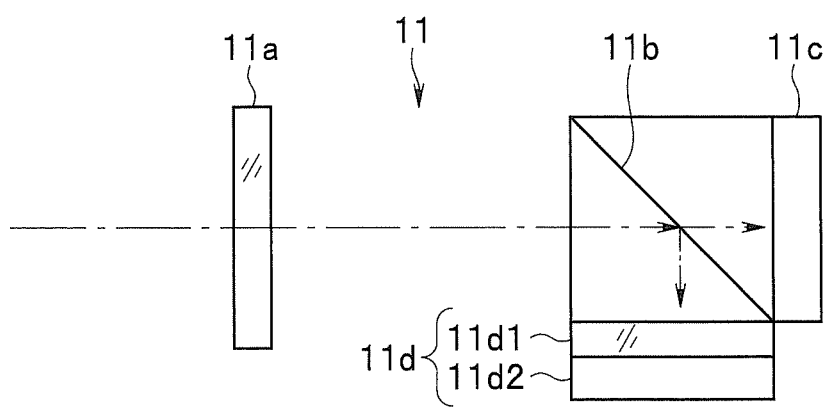
FIG. 2 is a diagram showing an example of a configuration of an image pickup section in an image pickup unit of a specific light observation endoscope that can perform observation using the normal light and the specific light in the first embodiment.

FIG. 2 is a diagram showing an example of a configuration of the image pickup section in the image pickup unit 11 of the specific light observation endoscope that can perform observation using the normal light and the specific light.

The image pickup section in the image pickup unit 11 includes an excitation light cutoff filter 11a, a beam splitter 11b, a normal light image pickup device 11c, and a specific light image pickup device 11d.

The excitation light cutoff filter 11a cuts off excitation light included in reflected light from the subject.

The beam splitter 11b splits light having passed through the excitation light cutoff filter 11a into two light beams and allows one of the light beams to arrive at the normal light image pickup device 11c and the other light beam to arrive at the specific light image pickup device 11d.

The normal light image pickup device 11c is configured as, for example, a monochrome image pickup device and, when an R light, a G light, and a B light, which create a white light as the normal light, are applied in a frame-sequential manner, outputs respective color images in a frame-sequential manner. An example using a frame-sequential method is described here, but the example is not restrictive, and a simultaneous method may be used by configuring the normal light image pickup device 11c by using, for example, a color image pickup device in which a primary-color Bayer filter is arranged.

In the present embodiment, an infrared light (an infrared light generated by the specific light observation light source apparatus 30) is used for the specific light, and a configuration is made such that observation of fluorescence from a subject is performed by irradiating the subject with the infrared light as an excitation light. Accordingly, the specific light image pickup device 11d is a device configured to pick up a fluorescence image from a subject irradiated with the specific light.

More specifically, the specific light image pickup device 11d in the present embodiment is configured by combining, for example, a fluorescence transmitting filter 11d1 that allows only fluorescence band light to pass through and a monochrome image pickup device 11d2.

The electrical signal acquired by such an image pickup unit 11 performing image pickup is sent to a video processing section 28, which will be described later, provided within the normal light source apparatus 20.

The illumination lens 12 is a lens arranged at the distal end portion of the insertion portion 19 of the specific light observation endoscope 10A and configured to radiate the normal light transmitted along the light guide 13 or the specific light transmitted along the specific light guide 14 toward a subject.

The light guide 13 is a first light guide portion connected to a connector receptacle 20b via the universal connector 16 and configured to guide the normal light from the normal light source apparatus 20 and to emit the normal light from an exit face at a distal end. The light guide 13 is configured as, for example, an optical fiber bundle formed by bundling a plurality of optical fibers and is inserted in the insertion portion 19 of the specific light observation endoscope 10A up to the distal end portion.

The specific light guide 14 is a second light guide portion configured to guide the specific light provided from a first IR-LD 33a and a second IR-LD 33b, which are specific light sources in the specific light observation light source apparatus 30, and to emit the specific light from an exit face at a distal end. The specific light guide 14 is configured by using a single optical fiber, an optical fiber bundle (a light guide) formed by bundling a plurality of optical fibers, or the like and, for example, is randomly mixed with the above-described light guide 13 on a distal end side. Accordingly, the exit face at the distal end of the light guide 13 and the exit face at the distal end of the specific light guide 14 are a common one. Thus, the normal light and the specific light irradiate a subject from the same place at the distal end portion of the insertion portion 19 via the illumination lens 12.

The scope ID memory 15 is a storage section configured to store identification information on the specific light observation endoscope 10A in a nonvolatile manner. The scope ID memory 15 stores information, such as a product model number and a manufacturing serial number of the specific light observation endoscope 10A, and a color balance value indicating a light amount ratio between a plurality of types of lights having different spectra. Here, the color balance value is, for example, a light amount ratio between the white light and the infrared light, or light amount proportions of the individual RGB lights in the white light, or further a light amount ratio between the G light and V light in the narrow band observation (Narrow Band Imaging: NBI (registered trademark)) mode, which will be described later, or the like. A configuration is made such that the information stored in the scope ID memory 15 is read by the video processing section 28 through a signal line.

The universal connector 16 is provided at a proximal end of a universal cord of the specific light observation endoscope 10A, and is a connector for connecting the specific light observation endoscope 10A to the connector receptacle 20b of the normal light source apparatus 20. The image pickup unit 11 and the scope ID memory 15 are connected to the video processing section 28 through the universal connector 16 and the connector receptacle 20b, so that the normal light is supplied to the light guide 13.

The specific light splitter cord 17 is, for example, a cord extended independently of the universal cord from an operation portion for allowing the specific light observation endoscope 10A to be operated, and including the specific light guide 14. However, such a configuration is not restrictive, and the specific light splitter cord 17 may be branched off from a midpoint of the universal cord or may be branched off from the universal connector 16.

The specific light connector 18 is provided at a proximal end of the specific light splitter cord 17 and is a connector for connecting the specific light observation endoscope 10A to a connector receptacle 30a of the specific light observation light source apparatus 30. A configuration is made such that the specific light is supplied from the specific light observation light source apparatus 30 to the specific light guide 14 via the specific light connector 18 and the connector receptacle 30a.

The insertion portion 19 is an elongated portion extended from the operation portion of the specific light observation endoscope 10A and configured to be inserted into a living subject. The light guide 13 and the specific light guide 14 are internally arranged in the insertion portion 19, and the insertion portion 19 is configured to emit the normal light guided by the light guide 13 and the specific light guided by the specific light guide 14 from a distal end of the insertion portion 19.

The normal light source apparatus 20 is a normal light observation light source apparatus including a housing 20a and, in the present embodiment, concurrently functions as a video processor for processing an image acquired from the image pickup unit 11. However, needless to say, the normal light source apparatus 20 may be configured independently of the video processor.

In the housing 20a, the connector receptacle 20b is provided that is a connection portion to which the specific light observation endoscope 10A (see FIG. 1) or a normal endoscope 10B (see FIG. 3) to be inserted into a living subject is connected.

The normal light source apparatus 20 includes, within the housing 20a, light emitting devices of a plurality of colors as light sources, more specifically, a red LED (R-LED) 23r that is a red (R) light emitting device, a green LED (G-LED) 23g that is a green (G) light emitting device, a blue LED (B-LED) 23b that is a blue (B) light emitting device, and a violet LED (V-LED) 23v that is a violet (V) light emitting device.

Of the light emitting devices, at least the red LED 23r, the green LED 23g, and the blue LED 23b are included in a normal light source that generates the normal light, so that lights emitted from such light emitting devices can create the white light as the normal light. Here, for respective color bands of red, green, and blue that are three primary colors creating the white light, the red band can be configured from the light emitted from the red LED 23r, the green band can be configured from the light emitted from the green LED 23g, and the blue band can be configured from the light emitted from the blue LED 23b.

However, by allowing the normal light source to further include the violet LED 23v, the blue band may be configured from both the light emitted from the blue LED 23b and a light emitted from the violet LED 23v.

A configuration is made such that the normal light thus generated passes through the specific light observation endoscope 10A or the normal endoscope 10B connected to the connector receptacle 20b and is emitted toward a living subject.

Incidentally, it is known that when light with narrow-band wavelengths that is easily absorbed by hemoglobin in blood is applied, blood vessels are observed in an emphasized manner. The violet LED 23v in the present embodiment is provided to perform such narrow band observation and is configured to emit, for example, narrow band light with wavelengths of 390 to 445 nm. When narrow band observation using the violet LED 23v is performed, for example, capillaries on a mucosal surface can be observed in an emphasized manner. In addition, it is known that when observation using narrow band light with wavelengths of 530 to 550 nm is performed, a contrast between observation of thick blood vessels located deeper and the capillaries on the mucosal surface can be emphasized. Accordingly, the green LED 23g in the present embodiment is configured to be able to generate the green light G for irradiating a living subject with such narrow band light.

The LED drive section 22 provided in the normal light source apparatus 20 is a section configured to drive the red LED 23r, the green LED 23g, the blue LED 23b, and the violet LED 23v by supplying a driving current to each of the LEDs 23r, 23g, 23b, and 23v.

The normal light source apparatus 20 is further provided with, as emission intensity detection sections configured to detect respective emission intensities of the light emitting devices of the plurality of colors, a photosensor 27r configured to detect the emission intensity of the red LED 23r, a photosensor 27g configured to detect the emission intensity of the green LED 23g, a photosensor 27b configured to detect the emission intensity of the blue LED 23b, and a photosensor 27v configured to detect the emission intensity of the violet LED 23v. Each of the photosensors 27r, 27g, 27b, and 27v outputs a result of detecting the emission intensity to the light source control section (light source controller) 21.

The light source control section 21 provided in the normal light source apparatus 20 adjusts the emission intensities of and color balances among the LEDs 23r, 23g, 23b, and 23v of the individual colors by controlling the LED drive section 22 based on the results of detection by the photosensors 27r, 27g, 27b, and 27v. The control of the LEDs 23r, 23g, 23b, and 23v of the individual colors by the normal light source apparatus 20 is configured to be performed through current light adjustment and PWM light adjustment in combination, which will be described later.

The normal light source apparatus 20 is provided with, as an optical system configured to guide and select an illumination light, four collimator lenses 24r, 24g, 24b, and 24v, three dichroic filters 25a, 25b, and 25c, an observation mode switch section 26, and a collector lens 24d.

The four collimator lenses 24r, 24g, 24b, and 24v are lenses arranged in optical paths of the respective outgoing lights from the red LED 23r, the green LED 23g, the blue LED 23b, and the violet LED 23v, respectively, and configured to emit the respective incident lights as parallel lights.

The first dichroic filter 25a is a filter configured to allow the red light R from the red LED 23r to pass through, and to reflect the green light G from the green LED 23g.

The second dichroic filter 25b is a filter configured to allow the red light R from the red LED 23r and the green light G from the green LED 23g to pass through, and to reflect the blue light B from the blue LED 23b.

The third dichroic filter 25c is a filter configured to allow the red light R from the red LED 23r, the green light G from the green LED 23g, and the blue light B from the blue LED 23b to pass through, and to reflect the violet narrow band light V from the violet LED 23v.

The observation mode switch section 26 is a section configured in such a manner that optical filters corresponding to the observation modes are arranged on a rotatable turret and the turret is rotated by a drive source such as a motor. For example, in normal observation, an opening state with no optical filter placed in is made, and in narrow band observation, a bandpass filter is configured that allows the light from the violet LED 23v to pass through and generates a narrow band G light required for narrow band observation from the wide band green light G from the green LED 23g.

Note that if the LEDs 23r, 23g, 23b, and 23v of the individual colors are configured to emit light simultaneously, a required color or required colors of light are selected by using the observation mode switch section 26, but if the LEDs 23r, 23g, 23b, and 23v of the individual colors are configured to emit light sequentially, a configuration omitting the observation mode switch section 26 may be adopted.

The collector lens 24d is a lens configured to collect a bundle of the parallel lights having passed through the observation mode switch section 26 on an incident end face at a proximal end of the above-described light guide 13.

An operation panel 29 provided in the normal light source apparatus 20 is a panel for allowing a user to operate the normal light source apparatus 20, so that the user can make operations such as turning on/off the normal light source apparatus 20 and setting an observation mode. A configuration is made such that an observation mode inputted from the operation panel 29 is sent to the video processing section 28 via the light source control section 21, and image processing corresponding to the observation mode is performed.

The video processing section 28 is configured to generate a color image signal by synchronizing images of the individual colors received from the image pickup unit 11, to convert the color image signal into a signal form for display after performing image processing such as color balance adjustment, gamma conversion, and color conversion, and to output the color image signal to a monitor or the like (not shown).

Here, the video processing section 28 is configured not only to perform image processing corresponding to the white light observation mode and the narrow band observation mode that can be set by using only the normal light source apparatus 20, but also to be able to perform image processing corresponding to the fluorescence observation mode (more generally, image processing corresponding to a specific light observation mode) that can be set when the specific light observation light source apparatus 30, which is an external light source, is connected.

Subsequently, the light source control section 21 acquires the color balance value stored in the scope ID memory 15 via the video processing section 28 and performs color balance adjustment of the illumination light.

For example, in the white light observation mode, the light source control section 21 adjusts an emission intensity balance among the red LED 23r, the green LED 23g, and the blue LED 23b (or between the blue LED 23b and the violet LED 23v).

In the narrow band observation mode, the light source control section 21 adjusts an emission intensity balance between the green LED 23g and the violet LED 23v.

In the fluorescence observation mode, the light source control section 21 outputs a light amount control signal that controls a light amount of the specific light to the specific light observation light source apparatus 30.

In other words, the light source control section 21 is a generation section configured to generate a light amount control signal that makes the light amount of the specific light have a predetermined light amount ratio to a light amount of the normal light, and is also an output section configured to output the light amount control signal that controls the light amount of the specific light to the specific light observation light source apparatus 30.

In such an event, the light source control section 21 is configured, in a first specific light observation mode (for example, in a first fluorescence observation mode), to generate and output a light amount control signal that makes a ratio of a light amount of a first specific light to the light amount of the normal light become a light amount ratio corresponding to the first specific light observation mode and, in a second specific light observation mode (for example, in a second fluorescence observation mode), to generate and output a light amount control signal that makes a ratio of a light amount of a second specific light to the light amount of the normal light become a light amount ratio corresponding to the second specific light observation mode.

Further, the light source control section 21 is configured to check with an LD light source control section 31, which will be described later, of the specific light observation light source apparatus 30 on communication and to determine that communication with the specific light observation light source apparatus 30 is enabled when a response is received from the LD light source control section 31, but determine that communication with the specific light observation light source apparatus 30 is disabled when no response is received from the LD light source control section 31. The light source control section 21 is configured to perform processing of generating and outputting the light amount control signal when communication with the specific light observation light source apparatus 30 is enabled, and to perform processing of not outputting the light amount control signal (although it is preferable that the light amount control signal is not even generated when the light amount control signal is not outputted in view of reducing power consumption, it is acceptable that the light amount control signal is generated but is not outputted) when communication with the specific light observation light source apparatus 30 is disabled.

The specific light observation light source apparatus 30 is an external light source provided outside the housing 20a of the normal light source apparatus 20, and is a light source apparatus that can generate and supply the specific light having the different spectrum from the spectrum of the normal light to the specific light observation endoscope 10A connected to the connector receptacle 20b.

Here, the specific light is a light that cannot be emitted by the normal light source apparatus 20 in principle. In other words, it is assumed that the white light, which is the normal light, is created from, for example, three RGB colors of lights. In such a case, it is assumed that spectra of the three RGB colors of lights are denoted as $R(\lambda)$, $G(\lambda)$, and $B(\lambda)$, respectively, where $\lambda$ represents a wavelength.

In such a case, if three coefficients kr, kg, and kb that take a positive value or 0 are used, a light that can be emitted by the normal light source apparatus 20 can be expressed in a form of linear combination as follows:

$$kr \times R(\lambda) + kg \times G(\lambda) + kb \times B(\lambda).$$

In contrast, when the coefficients kr, kg, and kb cannot be matched with a spectrum $X(\lambda)$ of the specific light however the value of each of the coefficients kr, kg, and kb is adjusted in a range of positive values or 0, it is assumed that X is referred to as the specific light. Note that even if violet $V(\lambda)$ is further included in the normal light, it is only necessary to add "$+kv \times V(\lambda)$" using a coefficient kv to the above-mentioned linear combination, and a similar definition can be used.

In the present embodiment, a narrow band infrared light emitted by an infrared laser (note that a bandwidth of laser light is narrower than a bandwidth of LED light in general) is used for the specific light. Here, since wavelengths of the excitation light vary with medical agents used or the like, the excitation light is not limited to the infrared light but may be visible light, ultraviolet light, or the like.

In addition, although the specific light is used as the excitation light for fluorescent emission in the present embodiment, the specific light is not limited to such a use. For example, in the configuration in FIG. 1, the violet LED 23v used for NBI illumination is provided within the normal light source apparatus 20. However, instead of such a configuration, the violet LED 23v may be provided within the specific light observation light source apparatus 30 (in such a case, the specific light is an NBI illumination light).

The specific light observation light source apparatus 30 in the present embodiment includes a plurality of infrared laser diodes (IR-LDs) having different wavelengths as light sources, more specifically, a first IR-LD 33a that emits an infrared narrow band light with a first wavelength and a second IR-LD 33b that emits an infrared narrow band light with a second wavelength different from the first wavelength.

Here, the first IR-LD 33*a* and the second IR-LD 33*b* are specific light sources configured to generate the specific light to be supplied to the specific light observation endoscope 10A. The first IR-LD 33*a* is a first specific light source configured to generate a first specific light corresponding to the first specific light observation mode, and the second IR-LD 33*b* is a second specific light source configured to generate a second specific light corresponding to the second specific light observation mode.

A reason for providing the plurality of infrared laser diodes is that different types of medical agents can be supported. Accordingly, one type of infrared laser diode may be provided, or three or more types of infrared laser diodes may be provided, or a light source or light sources that emit the excitation light other than the infrared light may be provided as mentioned above.

An LD drive section 32 provided in the specific light observation light source apparatus 30 is a section configured to drive the first IR-LD 33*a* and the second IR-LD 33*b* by supplying a driving current to each of the IR-LDs 33*a* and 33*b*.

The specific light observation light source apparatus 30 is provided with, as an optical system configured to guide and select the specific light, two collimator lenses 34*a* and 34*b*, a dichroic filter 35*a*, a low-reflection mirror 35*b*, and a collector lens 34*c*.

The two collimator lenses 34*a* and 34*b* are lenses arranged in optical paths of the respective outgoing lights from the first IR-LD 33*a* and the second IR-LD 33*b*, respectively, and configured to emit the respective incident lights as parallel lights.

The dichroic filter 35*a* is a filter configured to allow the infrared light with the first wavelength from the first IR-LD 33*a* to pass through, and to reflect the infrared light with the second wavelength from the second IR-LD 33*b*.

The low-reflection mirror 35*b* is a mirror configured to reflect the infrared light from the dichroic filter 35*a* at a lower reflectance than a reflectance of a general semi-transmissive mirror. Here, by using the low-reflection mirror 35*b*, the infrared light entering the specific light guide 14 is configured to lose little intensity.

A photosensor 37 as an emission intensity detection section configured to detect an emission intensity of the specific light is arranged in a path of the reflected light from the low-reflection mirror 35*b* in the specific light observation light source apparatus 30. The photosensor 37 is configured to output a result of detecting the emission intensity to the LD light source control section 31.

The LD light source control section 31 provided in the specific light observation light source apparatus 30 is a specific light controller (a second light controller) and is configured to receive the light amount control signal for controlling the light amount of the specific light from the above-described light source control section 21. Here, the normal light source apparatus 20 and the specific light observation light source apparatus 30 may perform communication through a wired line, or may perform communication through a wireless link.

The LD light source control section 31 is a light amount control section configured to receive the light amount control signal as an input and to control the light amount of the specific light based on the light amount control signal in such a manner that the light amount of the specific light has a predetermined light amount ratio to the light amount of the normal light.

More specifically, the LD light source control section 31 is configured to control the LD drive section 32 based on the received light amount control signal and the result of detection by the photosensor 37, and to adjust emission intensities of the first IR-LD 33*a* and the second IR-LD 33*b*. Emission intensity control by the LD light source control section 31 is configured to be performed through current light adjustment and PWM light adjustment in combination, similarly to the emission intensity control by the light source control section 21.

The collector lens 34*c* is a lens configured to collect a bundle of the parallel lights having passed through the low-reflection mirror 35*b* on an incident end face at a proximal end of the specific light guide 14.

Figure 3:
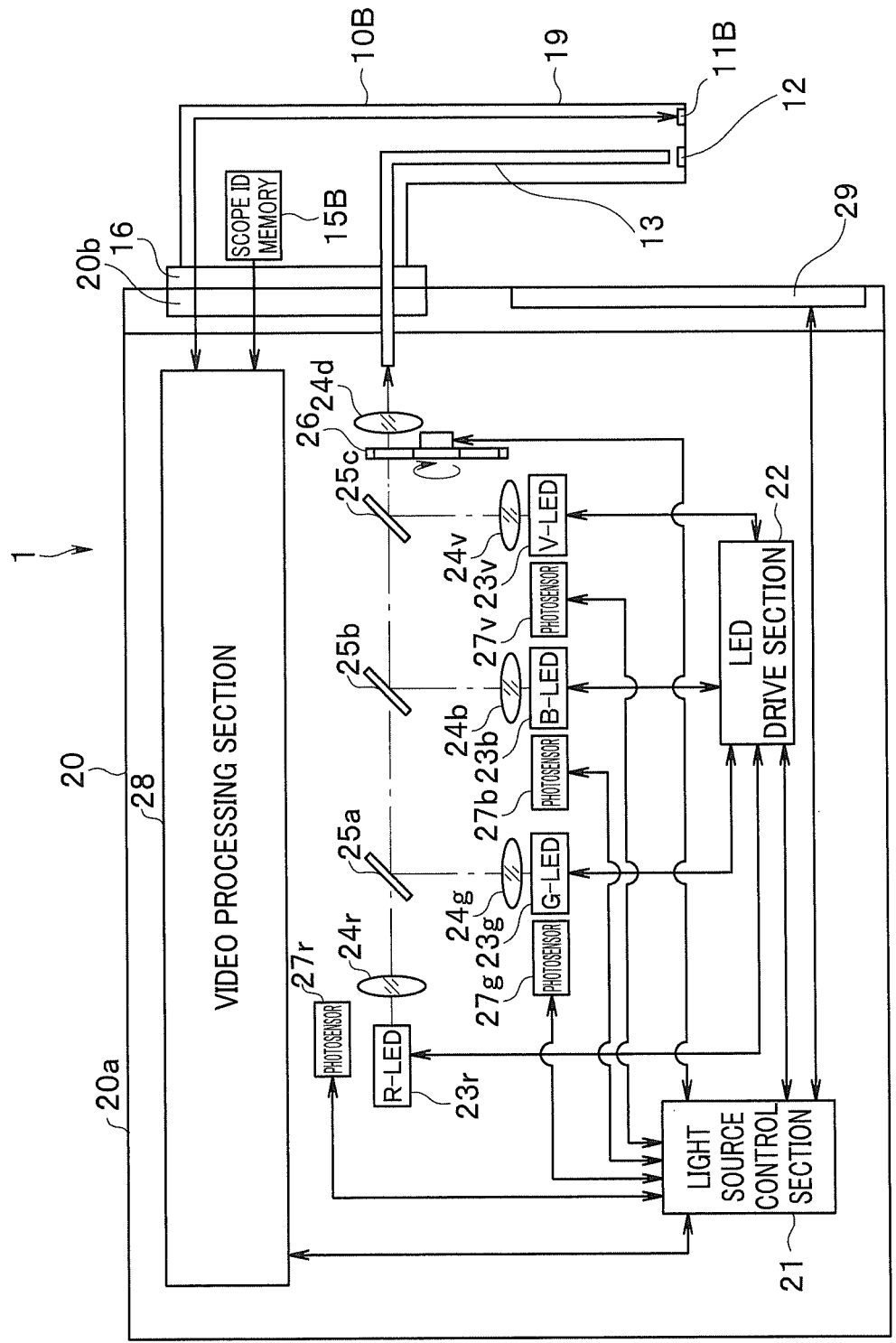
FIG. 3 is a diagram showing an example of the configuration of the endoscope system for performing observation using the normal light in the first embodiment.

Next, FIG. 3 is a diagram showing an example of a configuration of the endoscope system 1 for performing observation using the normal light, and FIG. 4 is a table showing combinations of apparatuses to be purchased by a user who performs only normal light observation and by a user who performs normal light observation and specific light observation.

A user who needs observation using the specific light builds the endoscope system 1 configured as shown in FIG. 1. In contrast, a user who does not need observation using the specific light may build the endoscope system 1 configured as shown in FIG. 3.

Here, the endoscope system 1 shown in FIG. 3 is configured by combining the normal endoscope 10B with the normal light source apparatus 20. Here, the normal light source apparatus 20 is the same as the normal light source apparatus 20 shown in FIG. 1.

The normal endoscope 10B is an endoscope for performing observation using the normal light that includes an image pickup unit 11B, the illumination lens 12, the light guide 13, a scope ID memory 15B, and the universal connector 16.

Here, the image pickup unit 11B is arranged at the distal end portion of the insertion portion 19 of the normal endoscope 10B, and includes an objective lens (not shown) configured to form an optical image of a subject irradiated with the normal light and an image pickup section configured to convert the optical image formed by the objective lens into an electrical signal. The image pickup section in the image pickup unit 11B is provided with only the normal light image pickup device 11*c*, by eliminating the excitation light cutoff filter 11*a*, the beam splitter 11*b*, and the specific light image pickup device 11*d* from the components shown in FIG. 2.

The scope ID memory 15B is a storage section configured to store identification information on the normal endoscope 10B in a nonvolatile manner. In other words, the scope ID memory 15B stores information, such as a product model number and a manufacturing serial number of the normal endoscope 10B, and a color balance value indicating a light amount ratio between a plurality of types of lights having different spectra. A configuration is made such that the information stored in the scope ID memory 15B is read by the video processing section 28 through a signal line.

As shown in FIG. 4, a user for whom performing only normal light observation suffices only needs to purchase a normal light observation light source apparatus, a video processing apparatus (which are integrated into the normal light source apparatus 20 in the present embodiment), and the normal endoscope 10B (apparatuses and an endoscope marked with ○ in FIG. 4 are to be purchased).

On the other hand, a user who performs normal light observation and specific light observation purchases a normal light observation light source apparatus and a video processing apparatus (the normal light source apparatus 20), the specific light observation light source apparatus 30, and the specific light observation endoscope 10A. Note that since the specific light observation endoscope 10A concurrently includes the functions of the normal endoscope 10B as described above, it is not necessary to additionally purchase the normal endoscope 10B.

Accordingly, in order for a user who already has the endoscope system 1 shown in FIG. 3 required for normal light observation to be able to further perform specific light observation, purchasing the specific light observation light source apparatus 30 and the specific light observation endoscope 10A will suffice. Since the specific light observation light source apparatus 30 is inexpensive compared to a light source apparatus that can emit both the normal light and the specific light, a transition to an environment where specific light observation is possible can be made at a relatively low cost.

Next, light amount control in the light source apparatus system 2 will be described with reference to FIGS. 5 to 8. FIG. 5 is a plot showing an example of a light amount of a first light source according to an emission time period and an emission intensity, and FIG. 6 is a plot showing an example of a light amount of a second light source according to an emission time period and an emission intensity.

Here, although the first light source and the second light source can be applied to any combination of light sources as long as the light sources are different from each other, it is assumed here, as an example, that the first light source is a light source that emits the normal light (for example, the G light as the reference light), and the second light source is a light source that emits the specific light (for example, the infrared narrow band light as described above). However, the first light source and the second light source may be the red LED 23$r$ and the green LED 23$g$, respectively, or the first light source and the second light source may be the green LED 23$g$ and the violet LED 23$v$, respectively, or further may be any other combination, and are not limited to examples described below.

Assuming that the emission time period and the emission intensity of the first light source during an exposure time period for one image (for example, an image of one frame) are $\tau 1$ and P1, respectively, the emitted light amount is expressed by P1×$\tau 1$ (an area of a rectangle shown in FIG. 5). Similarly, assuming that the emission time period and the emission intensity of the second light source during the exposure time period for one image are $\tau 2$ and P2, respectively, the emitted light amount is expressed by P2×$\tau 2$ (an area of a rectangle shown in FIG. 6).

The emission intensities P1 and P2 are changed by controlling a current value of a current supplied to the respective light sources, and the emission time periods $\tau 1$ and $\tau 2$ are changed by controlling a PWM duty of the current supplied to the respective light sources. Information about a light amount balance among color components included in the normal light is recorded in the scope ID memory 15, 15B, and information about a light amount balance between the normal light and the specific light is further recorded in the scope ID memory 15.

Since an intensity of fluorescence is low in general, the excitation light as the specific light needs to be able to secure a maximum light amount. Accordingly, when the second light source is made to produce the maximum light amount, a maximum emission time period $\tau 2$max of the second light source is set as $\tau 2$max=Texp where Texp is the exposure time period, and further a maximum current within a rated range is supplied to the second light source (the then emission intensity is assumed to be P2max).

It is necessary to determine a light amount of the normal light (for example, the reference light) in such a manner as to strike a balance with the fluorescence acquired from a subject when the excitation light having the maximum light amount (P2max×$\tau 2$max) is applied. Information indicating such a light amount ratio (a ratio between the light amount of the specific light and the light amount of the normal light) is the information about the light amount balance recorded in the scope ID memory 15.

As an example of the information about the light amount balance, a coefficient c can be recited that satisfies a following equation, which represents a ratio between the exposure time period Texp (=$\tau 2$max) and the emission time period $\tau 1$max of the first light source when the maximum current is supplied to the first light source:

$$\tau 2\text{max}=c\times\tau 1\text{max}.$$

Figure 7:
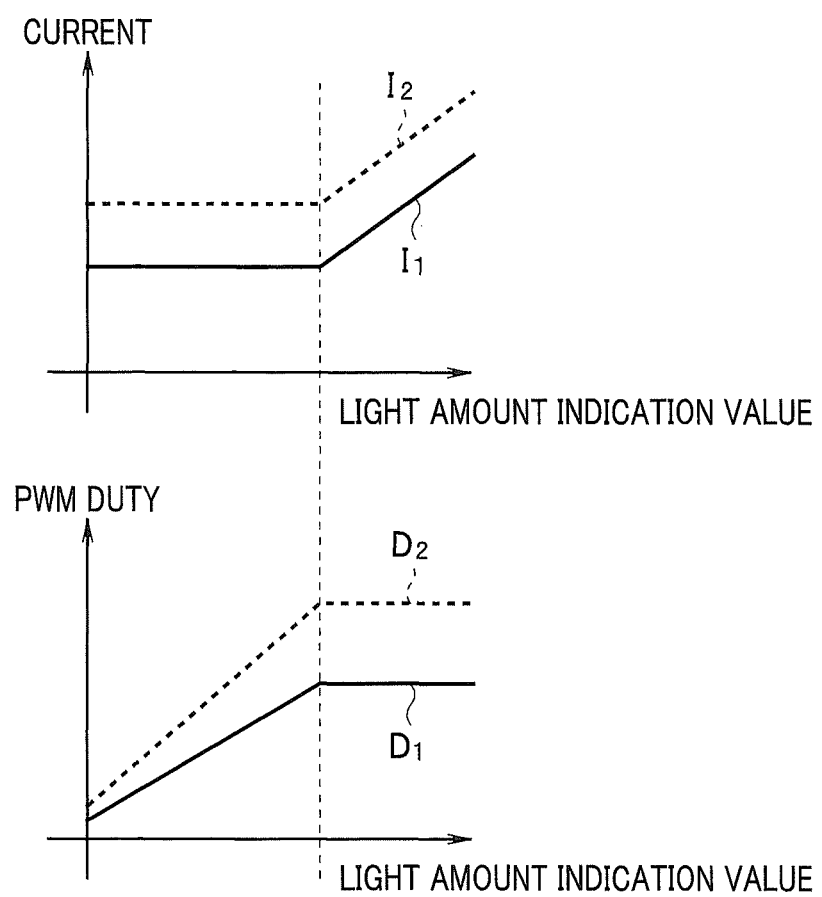
FIG. 7 is plots showing an example in which switching between current light adjustment and PWM light adjustment is made in accordance with a light amount indication value from a light source control section in the first embodiment.
Figure 8:
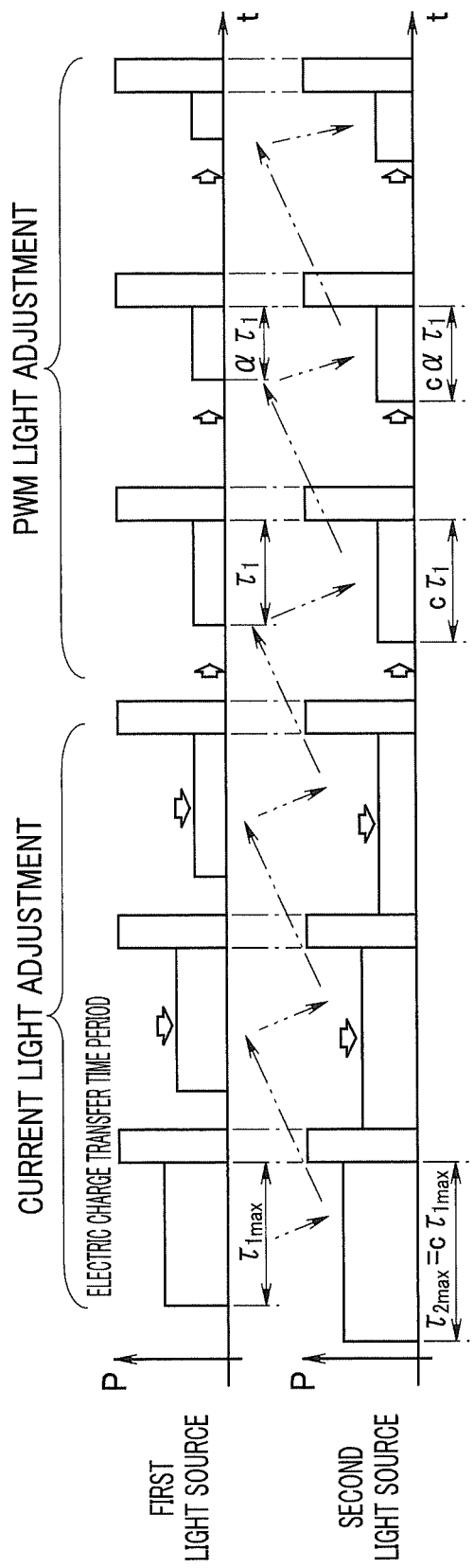
FIG. 8 is a diagram showing along a time axis how the switching between current light adjustment and PWM light adjustment is made in accordance with the light amount indication value from the light source control section in the first embodiment.

In case of reducing the emitted light amounts from emitted light amounts at a time of the maximum light amount, current light adjustment is configured to be performed first as shown in FIGS. 7 and 8. Here, FIG. 7 is plots showing an example in which switching between current light adjustment and PWM light adjustment is made in accordance with a light amount indication value from the light source control section 21, and FIG. 8 is a diagram showing along a time axis how the switching between current light adjustment and PWM light adjustment is performed in accordance with the light amount indication value from the light source control section 21.

When current light adjustment is entered, a current value I1 of the current supplied to the first light source and a current value I2 of the current supplied to the second light source are lowered while the emission time period $\tau 1$max of the first light source and the emission time period $\tau 2$max of the second light source are maintained. When the current light adjustment is performed, control of the current value I1 and the current value I2 is configured to be performed in such a manner as to keep P1/P2 that is a ratio between the emission intensities P1 and P2 at an arbitrary time detected by, for example, the photosensors 27$g$ and 37, respectively, equal to P1max/P2max that is a ratio between the emission intensities P1max and P2max at the time of the maximum light amount, that is, to maintain a following equation:

$$P1/P2=P1\text{max}/P2\text{max}.$$

Thereafter, for example, when either one of the current value I1 and the current value I2 reaches a minimum current value within a rated range (or a predetermined current value within the rated range may also be used), switching to PWM light adjustment is configured to occur as shown in FIG. 7.

Then, in the PWM light adjustment, PWM duties D1 and D2 are changed in such a manner as to maintain a ratio of the emission time periods, that is, to keep $\tau 1/\tau 2$ that is a ratio of the emission time periods $\tau 1$ and $\tau 2$ at an arbitrary time in the PWM light adjustment equal to $\tau 1$max/P$\tau$max that is a ratio between the emission time periods $\tau 1$max and $\tau 2$max at the time of the maximum light amount (and at the time of the current light adjustment), that is, to maintain a following equation:

$$\tau 1/\tau 2=\tau 1\text{max}/\tau 2\text{max}.$$

Here, in the present embodiment, since it is assumed that one current pulse is used to cause each light source to emit light during the exposure time period for one image (for example, an image of one frame), control of changing the PWM duties D1 and D2 is equivalent to control of changing the emission time periods $\tau 1$ and $\tau 2$ (if a plurality of current pulses (n current pulses) are used, control of changing the PWM duties D1 and D2 is control of changing the emission time periods τ1×n and τ2×n).

More specifically, when the emission time period of the first light source is τ1, the emission time period of the second light source is c×τ1. Similarly, when the emission time period of the first light source is α×τ1, the emission time period of the second light source is c×α×τ1.

Note that when a simultaneous-method configuration is used in which an image acquired when the normal light is emitted by the first light source and an image acquired when the specific light is emitted by the second light source can be acquired simultaneously, it is only necessary that the first light source and the second light source are caused to emit light simultaneously within the same frame time period, as shown in FIG. 8. In contrast, when a frame-sequential-method configuration is used in which an image acquired when the normal light is emitted by the first light source and an image acquired when the specific light is emitted by the second light source cannot be acquired simultaneously, it is only necessary that light emission by the first light source and light emission by the second light source are alternately performed for each frame, as shown with dashed double-dotted arrows in FIG. 8.

After exposure by causing the first and second light sources to emit light is finished, processing of transferring electric charge from the image pickup devices (the normal light image pickup device 11c and the specific light image pickup device 11d) and reading images is performed during an electric charge transfer time period after the light emission.

Figure 9:
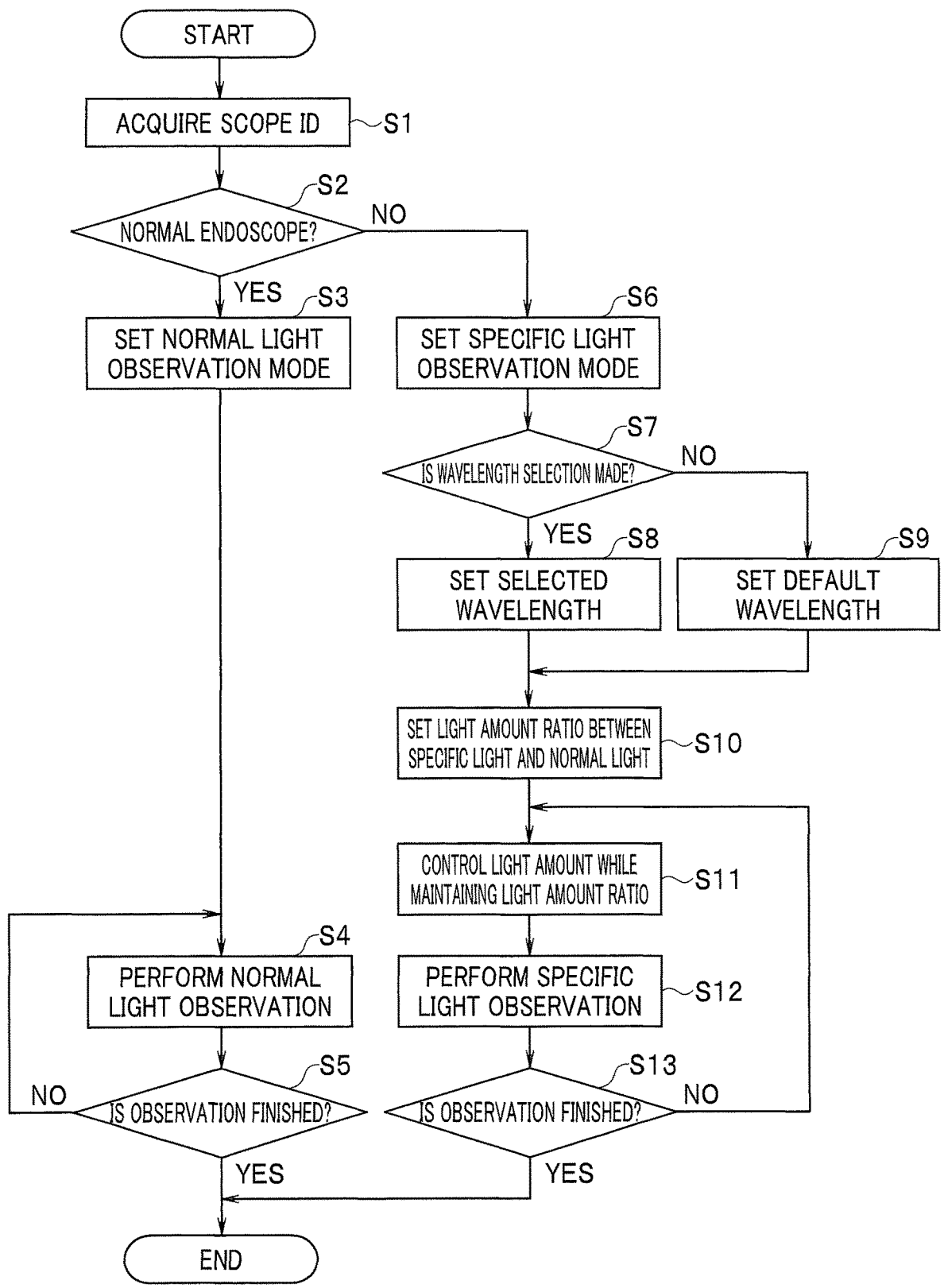
FIG. 9 is a flowchart showing operations of the endoscope system in the first embodiment.

FIG. 9 is a flowchart showing operations of the endoscope system 1.

When processing is started, the light source control section 21 acquires endoscope information (a scope ID) from the scope ID memory 15 via the video processing section 28 (step S1).

The light source control section 21 then determines, based on the acquired scope ID, whether an endoscope connected to the normal light source apparatus 20 is the normal endoscope 10B as shown in FIG. 3 or is the specific light observation endoscope 10A as shown in FIG. 1 (step S2).

Here, if it is determined that the endoscope is the normal endoscope 10B, the light source control section 21 sets the observation mode of the endoscope system 1 to the normal light observation mode (step S3).

Thereafter, normal light observation is performed by the endoscope system 1 as shown in FIG. 3 (step S4), and the light source control section 21 determines, at an appropriate time interval, whether or not the normal light observation is finished (step S5).

If it is determined here that the normal light observation is not finished, the processing returns to step S4 and the normal light observation is continued. If it is determined that the normal light observation is finished, the processing is terminated.

If it is determined in step S2 that the connected endoscope is the specific light observation endoscope 10A, the light source control section 21 sets the observation mode of the endoscope system 1 to the specific light observation mode (step S6).

The light source control section 21 then determines whether or not selection of a wavelength of the specific light to be used is made, more specifically, selection of which one of the first IR-LD 33a and the second IR-LD 33b is used is made by, for example, user operation through the operation panel 29 (step S7).

If it is determined here that selection is made, the light source control section 21 sends to the LD light source control section 31 a control signal that causes a light with the selected wavelength to be emitted (step S8). If it is determined that selection is not made, the light source control section 21 sends to the LD light source control section 31 a control signal that causes a light with a predetermined wavelength (a default wavelength) to be emitted (step S9).

When the processing in step S8 or step S9 is performed, the light source control section 21 sets the light amount ratio between the specific light emitted by the specific light observation light source apparatus 30 and the normal light emitted by the normal light source apparatus 20 as described above (step S10).

The light source control section 21 then controls the LED drive section 22 and also transmits a light amount control signal to the LD light source control section 31 to maintain the set light amount ratio (step S11). The above-described current light adjustment and PWM light adjustment are configured to be performed through such control.

Thereafter, specific light observation is performed by the endoscope system 1 as shown in FIG. 1 (step S12), and the light source control section 21 determines, at an appropriate time interval, whether or not the specific light observation is finished (step S13).

If it is determined here that the specific light observation is not finished, the processing returns to step S11, the light amount control is performed, and then the specific light observation is continued in step S12. If it is determined that the specific light observation is finished, the processing is terminated.

Note that although the normal light source apparatus 20 has a configuration including the LEDs of the plurality of colors in the above description, a configuration of the normal light source apparatus 20 to be combined with the specific light observation light source apparatus 30 is not limited to such a configuration. For example, the normal light source apparatus 20 may have a configuration using a xenon lamp.

According to the first embodiment as described above, the light source control section 21 of the normal light source apparatus 20 including the normal light source is configured to output the light amount control signal that controls the light amount of the specific light, and the LD light source control section 31 of the specific light observation light source apparatus 30 is configured to receive the light amount control signal as an input and, based on the light amount control signal, to control the light amount of the specific light in such a manner that the light amount of the specific light has the predetermined light amount ratio to the light amount of the normal light. Accordingly, if a user who performs observation using the normal light by using the normal light source apparatus 20 and the normal endoscope 10B intends to further perform observation using the specific light, purchasing the specific light observation endoscope 10A and the specific light observation light source apparatus 30, which is relatively inexpensive, will suffice. In other words, since it is not necessary to upgrade to an expensive light source apparatus that can generate both the normal light and the specific light, it is possible to perform specific light observation at lower costs than costs conventionally incurred.

Since the light source control section 21 is configured to output the light amount control signal when communication with the specific light observation light source apparatus 30 is enabled and not to output the light amount control signal when communication with the specific light observation light source apparatus 30 is disabled, the light amount control signal is not uselessly outputted when the specific light observation light source apparatus 30 is not connected or the like, and low power consumption can be achieved. When communication with the specific light observation light source apparatus 30 is disabled in particular, further low power consumption can be achieved if a configuration is made such that the light amount control signal itself is not generated.

Since the light source control section 21, which is a generation section, generates the light amount control signal that makes the light amount of the specific light have the predetermined light amount ratio to the light amount of the normal light, observation using the specific light can be performed at an appropriate light amount based on the normal light as the reference light.

When the light source control section 21 is configured to output the light amount control signal to the specific light observation light source apparatus 30 that supplies the specific light to the specific light observation endoscope 10A connected to the connector receptacle 20b, the normal light source apparatus 20 can be implemented at a lower cost because it is not necessary to provide the LD light source control section 31 or the like in the normal light source apparatus 20.

In addition, when the specific light observation light source apparatus 30 has a configuration including the first specific light source corresponding to the first specific light observation mode and the second specific light source corresponding to the second specific light observation mode, the light source control section 21, which is a generation section, is configured to generate the light amount control signal corresponding to any one of the specific light observation modes. Accordingly, observation can be performed at a light amount ratio suitable for each of a plurality of the specific light observation modes.

Since the specific light observation endoscope 10A includes the light guide 13 configured to guide the normal light and the specific light guide 14 configured to guide the specific light, it is possible to perform normal light observation and specific light observation with the single endoscope. Further, it is also possible to use the normal light for the reference light in the specific light observation mode.

Furthermore, since the emitted light amounts of the light sources are configured to be adjusted by current light adjustment and PWM light adjustment in combination, images under wide dynamic range illumination can be acquired.

Second Embodiment

Figure 10:
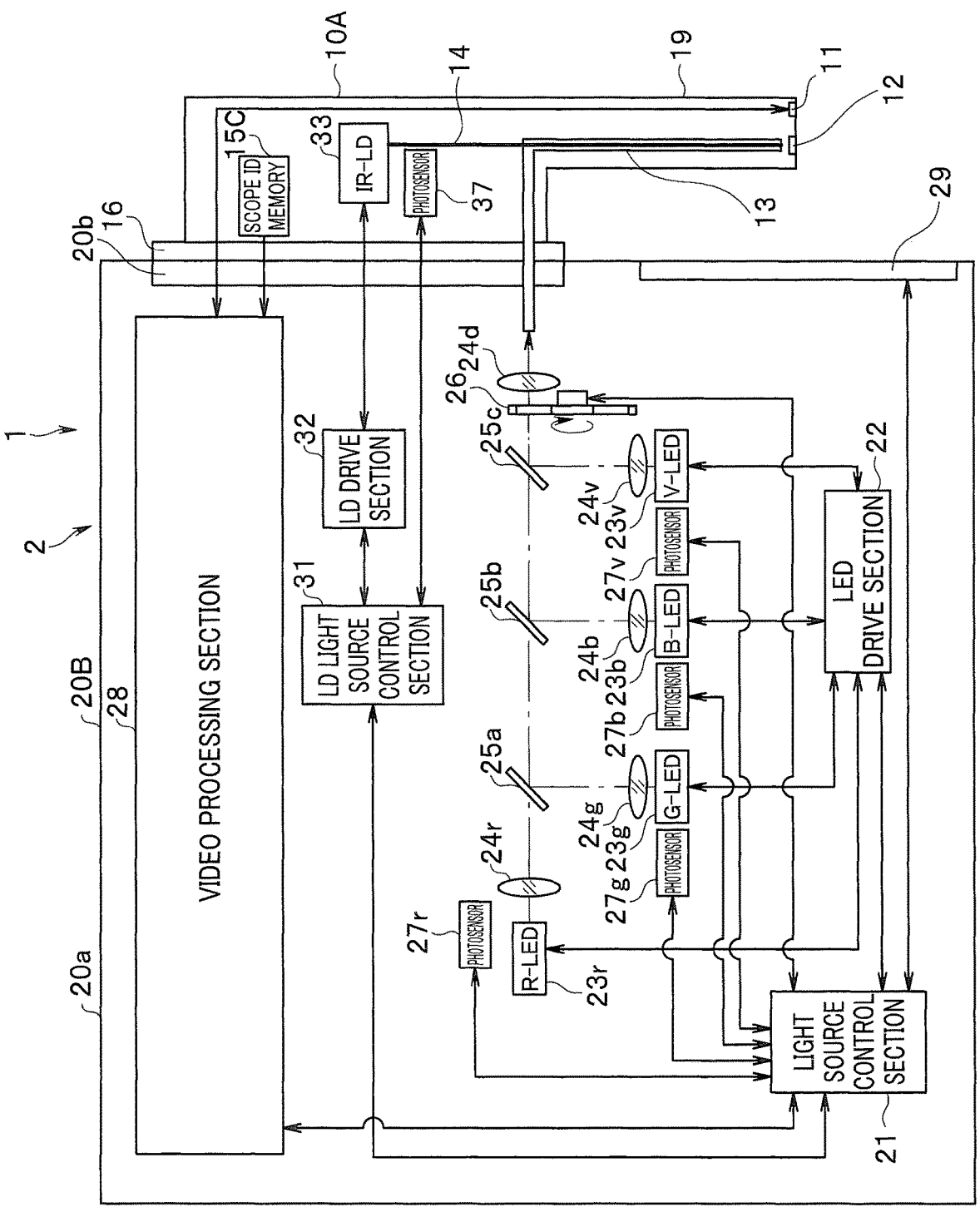
FIG. 10 is a diagram showing an example of a configuration of an endoscope system that can perform observation using the normal light and the specific light, according to a second embodiment of the present invention.
Figure 11:
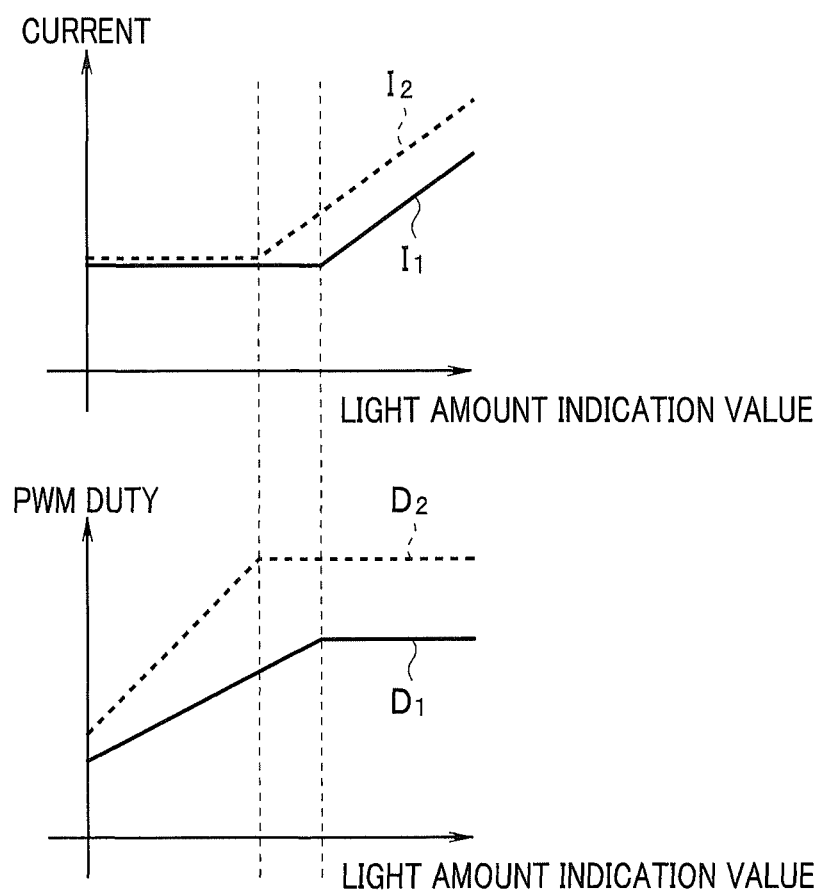
FIG. 11 is plots showing an example in which timing of switching between current light adjustment and PWM light adjustment is differentiated between a first light source and a second light source in the second embodiment.
Figure 12:
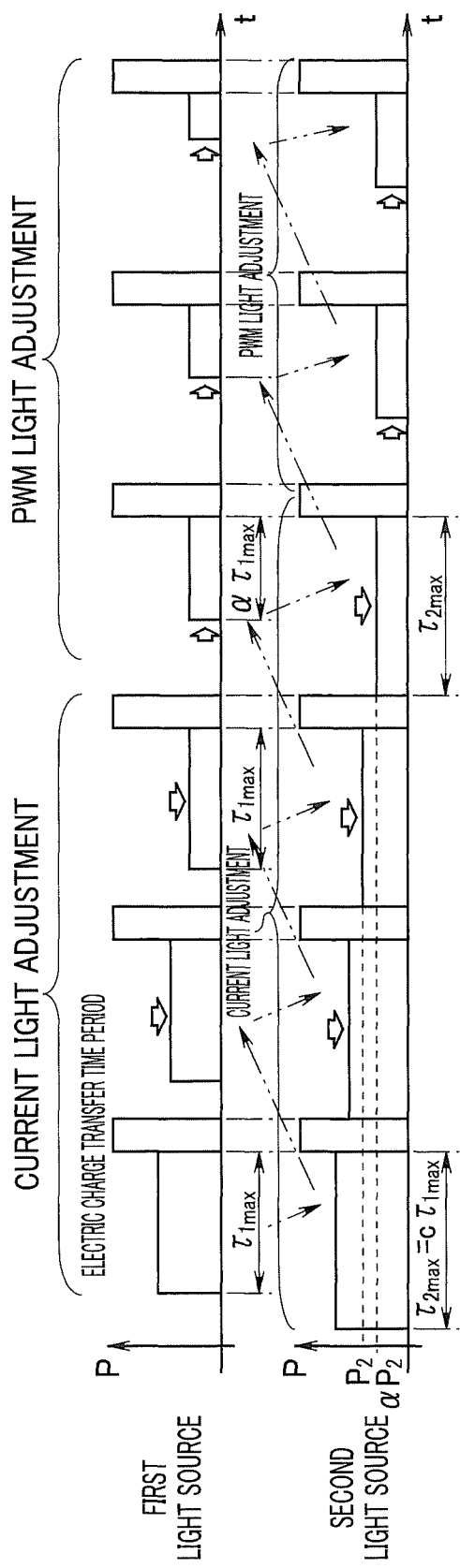
FIG. 12 is a diagram showing along a time axis how the timing of switching between current light adjustment and PWM light adjustment is differentiated between the first light source and the second light source in the second embodiment.

FIGS. 10 to 12 show a second embodiment of the present invention, and FIG. 10 is a diagram showing an example of a configuration of an endoscope system that can perform observation using the normal light and the specific light.

In the second embodiment, description of similar parts to the above-described first embodiment will be omitted as appropriate by denoting such parts by the same reference signs or the like, and only different points will mainly be described.

In the above-described first embodiment, a configuration is made such that the independent specific light observation light source apparatus 30 is provided outside the housing 20a of the normal light source apparatus 20. In the present embodiment, an independent specific light observation light source apparatus is eliminated by providing an IR-LD 33, which is a specific light source, within the specific light observation endoscope 10A to configure the specific light observation endoscope 10A itself to concurrently function as at least part of the specific light observation light source apparatus.

In other words, the IR-LD 33, which is an infrared laser diode, is provided within the specific light observation endoscope 10A in the present embodiment, and a configuration is made such that an infrared laser light generated by the IR-LD 33 is guided by the specific light guide 14.

A scope ID memory 15C provided within the specific light observation endoscope 10A stores identification information for identifying the specific light observation endoscope 10A that includes the IR-LD 33 and control information for controlling the IR-LD 33, in addition to a product model number, a manufacturing serial number, and the like as described above, in a nonvolatile manner.

Within a normal light source apparatus 20B in the present embodiment, the LD light source control section 31 and the LD drive section 32 are further provided in addition to the components of the normal light source apparatus 20 in the first embodiment. The light source control section 21 is connected to the IR-LD 33 via the LD light source control section 31 and the LD drive section 32.

Accordingly, the light source control section 21 is configured to output a generated light amount control signal to the LD light source control section 31 provided within the normal light source apparatus 20B.

Next, light amount control in the light source apparatus system 2 according to the present embodiment will be described with reference to FIGS. 11 and 12. FIG. 11 is plots showing an example in which timing of switching between current light adjustment and PWM light adjustment is differentiated between the first light source and the second light source, and FIG. 12 is a diagram showing along a time axis how the timing of switching between current light adjustment and PWM light adjustment is differentiated between the first light source and the second light source.

Although the timing of switching between current light adjustment and PWM light adjustment is the same for the first light source and the second light source in the previously described embodiment, such timing is differentiated in the present embodiment.

As described above, even if light amounts are changed, control is performed in such a manner that a light amount ratio between the first light source and second light source is kept constant.

For example, if the emitted light amounts are reduced from emitted light amounts at a time of a maximum light amount, current light adjustment is performed first (that is, the current supplied to the first light source and the current supplied to the second light source are reduced), as in the above-described first embodiment. At the time, even when one of the first light source and the second light source reaches a minimum current value within a rated range (or a predetermined current value within the rated range as described above), the other of the first light source and the second light source, in general, does not reach a minimum current value within a rated range (or, similarly, a predetermined current value within the rated range).

Accordingly, control is performed in such a manner that while adjustment is switched from the current light adjustment to PWM light adjustment for the light source that has reached the minimum current value (or the predetermined current value; the same will apply hereinafter), the current light adjustment is continued for the light source that does not reach the minimum current value.

More specifically, in the example shown in FIGS. 11 and 12, while adjustment is switched from the current light adjustment to PWM light adjustment for the first light source because the current value I1 supplied to the first light source first reaches the minimum current value, the current light adjustment is continually performed for the second light source until the current value I2 supplied to the second light source reaches the minimum current value.

During a period in which such different types of control are performed, for the first light source, the PWM duty D1 is changed while the current value I1 is maintained at the minimum current value, and for the second light source, the current value I2 is changed while the PWM duty D2 is kept constant.

Thereafter, when the current value I2 supplied to the second light source reaches the minimum current value, adjustment is also switched from the current light adjustment to PWM light adjustment for the second light source.

For example, assuming that the emission time period of the first light source and the emission intensity of the second light source when the current value I1 reaches the minimum current value are $\tau1max$ and P2, respectively, and that the emission intensity of the second light source when the current value I2 reaches the minimum current value is $\alpha \times P2$, the emission time period of the second light source when the current value I2 reaches the minimum current value is $\alpha \times \tau1max$ because the light amount ratio is kept constant.

After both the first light source and the second light source thus reach the respective minimum current values, light amount control of the first light source and the second light source is performed through the PWM light adjustment.

Note that the switching between current light adjustment and PWM light adjustment at a simultaneous timing described in the first embodiment may be applied to the configuration of the present embodiment, and the switching between current light adjustment and PWM light adjustment at different timings described in the present embodiment may be applied to the configuration of the first embodiment.

According to the second embodiment as described above, effects almost the same as the above-described effects of the first embodiment can be achieved. In addition, since the normal light source apparatus 20B is configured to include the LD light source control section 31, which is a light amount control section configured to control the light amount of the specific light, and the normal endoscope 10B is configured to include the IR-LD 33, which is a specific light source, the normal light source apparatus 20B concurrently functions as part of the specific light observation light source apparatus, and the normal endoscope 10B concurrently functions as other part of the specific light observation light source apparatus. Accordingly, it is not necessary to provide the specific light observation light source apparatus as a discrete single body independently of the normal light source apparatus 20B and the normal endoscope 10B, and the configuration can be simplified. As a result, since a smaller number of apparatuses are required when specific light observation is performed, work of connecting the apparatuses is made easier at a preparation stage prior to performing the specific light observation.

Even if the timing of switching between current light adjustment and PWM light adjustment is differentiated, images under wide dynamic rage illumination can be acquired as in the case of the same timing of switching.

Note that functions of the above-described individual sections may be configured to be implemented by one or more processors configured as hardware.

Although the above description is given mainly of the light source apparatus system, the normal light source apparatus, the specific light observation light source apparatus, and the endoscope system, the present invention may be an operation method that causes each apparatus and each system to operate as described above, or may be a processing program for causing a computer to perform processing similar to the processing performed by each apparatus and each system or a computer readable non-transient recording medium that records such a processing program, or the like.

The present invention is not limited to the above-described embodiments as they are, and the constituent elements may be embodied in changed forms without departing from the scope of the invention in the stage of carrying out the invention. Moreover, various aspects of the present invention can be formed by appropriately combining the plurality of constituent elements disclosed in the above-described embodiments. For example, some constituent elements may be eliminated from among all of the constituent elements disclosed in each embodiment. Further, constituent elements in the different embodiments may be combined as appropriate. Needless to say, various changes and applications can be made as described above without departing from the spirit of the invention.

What is claimed is:

1. A light source system configured to supply light to an endoscope, the light being emitted from the endoscope toward a subject, the light source system comprising:
   a normal light source apparatus provided within a housing and configured to be able to emit a normal light for being emitted toward the subject;
   a specific light source apparatus for specific light provided independently of the housing and configured to be able to emit, toward the subject, a specific light having a different spectrum from a spectrum of the normal light for being emitted toward the subject;
   a normal light source controller provided in the normal light source apparatus and configured to adjust an emission intensity of the normal light and to generate a light amount control signal that makes a light amount of the specific light have a predetermined light amount ratio to a light amount of the normal light; and
   a specific light controller provided in the specific light source apparatus and configured to adjust an emission intensity of the specific light,
   wherein in a state where communication between the normal light source apparatus and the specific light source apparatus is enabled, the normal light source controller adjusts the emission intensity of the normal light and sends the light amount control signal to the specific light source apparatus, and
   the specific light controller adjusts the emission intensity of the specific light based on the received light amount control signal.

2. The light source system according to claim 1, wherein the normal light is a green light as a reference light, and the specific light is an infrared light having a narrower band than the reference light.

3. The light source system according to claim 1, wherein the normal light source apparatus comprises a plurality of semiconductor light sources for creating the normal light, and normal light detection sensors configured to detect respective emission intensities of the plurality of semiconductor light sources.

4. The light source system according to claim 1, wherein the specific light source apparatus comprises a photosensor configured to detect the emission intensity of the specific light, and the specific light controller adjusts the emission intensity of the specific light based on the received light amount control signal and a result of detection by the photosensor.

5. The light source system according to claim 1, wherein the specific light source apparatus comprises a semiconductor light source for creating the specific light, and
the specific light controller is configured to switch between light adjustment using a current value and light adjustment using a pulse width for the semiconductor light source, based on the light amount control signal.

6. A light source control method of supplying a light to an endoscope, the light being emitted from the endoscope toward a subject, the light source control method comprising:
emitting a normal light for being emitted toward the subject from a normal light source apparatus provided within a housing;
emitting, toward the subject, a specific light having a different spectrum from a spectrum of the normal light toward the subject from a specific light source apparatus for specific light provided independently of the housing;
in a state where communication between the normal light source apparatus and the specific light source apparatus is enabled,
adjusting an emission intensity of the normal light by a normal light source controller provided in the normal light source apparatus, generating by the normal light source controller a light amount control signal that makes a light amount of the specific light have a predetermined light amount ratio to a light amount of the normal light, and sending the light amount control signal to the specific light source apparatus; and
receiving the light amount control signal by a specific light controller provided in the specific light source apparatus, and adjusting by the specific light controller an emission intensity of the specific light based on the light amount control signal.

7. A first light source apparatus that can generate a first light having a first spectral distribution to be emitted from an endoscope, toward a subject, and configured to supply the first light to the endoscope, the first light source apparatus comprising:
a housing;
a first light source provided within the housing and configured to emit the first light; and
a first light source controller provided within the housing and configured to adjust an emission intensity of the first light source,
wherein the first light source apparatus can communicate with a second light source apparatus provided outside the housing and configured to supply a second light to the endoscope, the second light source apparatus including a second light source configured to emit the second light for being emitted from the endoscope toward the subject, the second light having a second spectral distribution different from the first spectral distribution and a second light controller configured to adjust an emission intensity of the second light source, and in a state where communication between the first light source apparatus and the second light source apparatus is enabled,
the first light source controller adjusts the emission intensity of the first light source, and
sends to the second light source apparatus a light amount control signal for allowing the second light controller to control the second light source and for adjusting the emission intensity of the second light in such a manner as to make a light amount of the second light have a predetermined light amount ratio to a light amount of the first light.

8. An endoscope system comprising:
a first light source apparatus provided within a housing and configured to be able to emit a first light having a first spectral distribution for being emitted from an endoscope toward a subject;
a second light source apparatus provided independently of the housing and configured to be able to emit a second light for being emitted from the endoscope toward the subject, the second light having a second spectral distribution different from the first spectral distribution;
an endoscope connected to the first light source apparatus and the second light source apparatus and configured to be supplied with the first light and the second light to be emitted toward the subject;
a first light source controller provided in the first light source apparatus and configured to adjust an emission intensity of the first light and to generate a light amount control signal that makes a light amount of the second light have a predetermined light amount ratio to a light amount of the first light; and
a second light controller provided in the second light source apparatus and configured to adjust an emission intensity of the second light,
wherein in a state where communication between the first light source apparatus and the second light source apparatus is enabled, the first light source controller adjusts the emission intensity of the first light and sends the light amount control signal to the second light source apparatus, and
the second light controller adjusts the emission intensity of the second light based on the received light amount control signal.

9. The light source system according to claim 1, wherein the normal light controller is configured to acquire a color balance value stored in a memory in the endoscope to perform color balance adjustment of the normal light.

10. The light source control method according to claim 6, wherein the normal light controller is configured to acquire a color balance value stored in a memory in the endoscope to perform color balance adjustment of the normal light.

11. The first light source apparatus according to claim 7, wherein the first light source controller is configured to acquire a color balance value stored in a memory in the endoscope to perform color balance adjustment of the first light.

12. The endoscope system according to claim 8, wherein:
the endoscope further comprises a memory storing a color balance value; and
the first light controller is configured to acquire the color balance value from the endoscope and perform color balance adjustment of the normal light.

* * * * *